US00PP18481P2

(12) United States Plant Patent
Dümmen

(10) Patent No.: US PP18,481 P2
(45) Date of Patent: Feb. 12, 2008

(54) ***OSTEOSPERMUM* PLANT NAMED 'DUETISUNEYE'**

(50) Latin Name: *Osteospermum ecklonis*
Varietal Denomination: Duetisuneye

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 90 days.

(21) Appl. No.: 11/349,641

(22) Filed: Feb. 7, 2006

(51) Int. Cl.
*A01H 5/00* (2006.01)

(52) U.S. Cl. ..... Plt./360

(58) Field of Classification Search ..... Plt./360
See application file for complete search history.

(56) References Cited

PUBLICATIONS

UPOV ROM GTITM Computer Database, GTI Jouve Retrieval Softwear 2006/05, Citation for 'Duetisuneye'.*

* cited by examiner

*Primary Examiner*—Wendy Haas
(74) *Attorney, Agent, or Firm*—C. A. Whealy

(57) ABSTRACT

A new and distinct cultivar of *Osteospermum* plant named 'Duetisuneye', characterized by its compact and uniformly mounded plant habit; freely branching growth habit; full and dense plants; freely and early flowering habit; and large inflorescences with bright yellow-colored ray florets.

1 Drawing Sheet

Botanical designation: *Osteospermum ecklonis.*
Cultivar denomination: 'Duetisuneye'.

CROSS-REFERENCE TO RELATED APPLICATIONS

The present application is co-pending with the following related applications: Title: *Osteospermum* Plant Named 'Duetibredaor', U.S. Plant patent application Ser. No. 11/349,673 Applicant: Marga Dümmen Title: *Osteospermum* Plant Named 'Duetibreyech', U.S. Plant patent application Ser. No. 11/349,715 Applicant: Marga Dümmen.

BACKGROUND OF THE INVENTION

The present Invention relates to a new and distinct cultivar of *Osteospermum* plant, botanically known as *Osteospermum ecklonis,* and hereinafter referred to by the name 'Duetisuneye'.

The new *Osteospermum* is a product of a planned breeding program conducted by the Inventor in Rheinberg, Germany. The objective of the breeding program is to create new compact *Osteospermum* cultivars with uniform plant habit, early flowering and interesting floret coloration.

The new *Osteospermum* originated from a cross-pollination made by the Inventor in July, 2003 of a proprietary selection of *Osteospermum ecklonis* identified as code number F-03-19, not patented, as the female, or seed, parent with a proprietary selection of *Osteospermum ecklonis* identified as code number F-01-13, not patented, as the male, or pollen, parent. The new *Osteospermum* was discovered and selected by the Inventor as a single flowering plant within the progeny of the stated cross-pollination grown in a controlled environment in Rheinberg, Germany in July, 2004.

Asexual reproduction of the new *Osteospermum* by vegetative tip cuttings was first conducted in Rheinberg, Germany in July, 2004. Asexual reproduction by cuttings has shown that the unique features of this new *Osteospermum* are stable and reproduced true to type in successive generations.

SUMMARY OF THE INVENTION

The cultivar Duetisuneye has not been observed under all possible environmental conditions. The phenotype may vary somewhat with variations in environment such as temperature and light intensity without, however, any variance in genotype.

The following traits have been repeatedly observed and are determined to be the unique characteristics of 'Duetisuneye'. These characteristics in combination distinguish 'Duetisuneye' as a new and distinct *Osteospermum:*

1. Compact and uniformly mounded plant habit.
2. Freely branching growth habit; full and dense plants.
3. Freely and early flowering habit.
4. Large inflorescences with bright yellow-colored ray florets.

Plants of the new *Osteospermum* differ primarily from plants of the parent selections in ray floret color as plants of both parent selections have paler yellow-colored ray florets. In addition, plants of the new *Osteospermum* are more compact than plants of the parent selections.

Plants of the new *Osteospermum* differ primarily from plants of the cultivar Duetibredaor, disclosed in U.S. Plant patent application Ser. No. 11/349,673, and the cultivar Duetibreyech, disclosed in U.S. Plant patent application Ser. No. 11/349,715, in ray floret color.

Plants of the new *Osteospermum* can be compared to plants of the *Osteospermum* cultivar Countryside, not patented. In side-by-side comparisons conducted in Rheinberg, Germany, plants of the new *Osteospermum* differed from plants of the cultivar Countryside in the following characteristics:

1. Plants of the new *Osteospermum* were more compact than plants of the cultivar Countryside.
2. Plants of the new *Osteospermum* were more freely branching than plants of the cultivar Countryside.
3. Plants of the new *Osteospermum* had smaller leaves with shorter petioles than plants of the cultivar Countryside.
4. Plants of the new *Osteospermum* and the cultivar Countryside differed in ray floret coloration as plants of the cultivar Countryside had pale yellow-colored ray florets.

BRIEF DESCRIPTION OF THE PHOTOGRAPH

The accompanying colored photograph illustrates the overall appearance of the new *Osteospermum* showing the colors as true as it is reasonably possible to obtain in colored reproductions of this type. Colors in the photograph may differ from the color values cited in the detailed botanical description which accurately describe the colors of the new *Osteospermum.* The photograph comprises a side perspective view of a typical flowering plant of 'Duetisuneye' grown in container.

DETAILED BOTANICAL DESCRIPTION

In the following description, color references are made to The Royal Horticultural Society Colour Chart, 1995 Edition, except where general terms of ordinary dictionary significance are used. The aforementioned photograph, following observations and measurements describe plants grown during the spring in Rheinberg, Germany, in a glass-covered greenhouse and under conditions which approximate those generally used in commercial *Osteospermum* production. Single plants were grown in 13-cm containers and pinched about one week after planting. During the production of the plants, day and night temperatures were about 18° C. and light levels were about 4,500 foot-candles. Plants used in the photograph and for the botanical description were about four months old.

Botanical classification: *Osteospermum ecklonis* cultivar Duetisuneye.

Parentage:

*Female, or seed, parent.*—Proprietary selection of *Osteospermum ecklonis* identified as code number F-03-19, not patented.

*Male, or pollen, parent.*—Proprietary selection of *Osteospermum ecklonis* identified as code number F-01-13, not patented.

Propagation:

*Type.*—Terminal cuttings.

*Time to initiate roots, summer and winter.*—About 10 days at 20° C.

*Time to develop roots, summer and winter.*—About three weeks at 20° C.

*Root description.*—Fibrous, fine; white in color.

*Rooting habit.*—Freely branching.

Plant description:

*Appearance.*—Perennial herbaceous container and garden plant. Compact and uniformly mounded plant habit; upright and somewhat outwardly spreading; inverted triangle. Freely branching, about four to six primary lateral branches; dense and full plants. Moderately vigorous growth habit.

*Plant height.*—About 16.5 cm.

*Plant width or area of spread.*—About 15 cm.

*Lateral branches.*—Length: About 15 cm. Diameter: About 5 mm. Internode length: About 5 mm. Strength: Strong. Texture: Glabrous, smooth. Color: 144B.

*Foliage description.*—Arrangement: Alternate; simple. Length: About 8 cm. Width: About 2 cm. Shape: Spatulate. Apex: Acute. Base: Attenuate. Margin: Dentate; sinuses divergent. Venation pattern: Pinnate. Texture, upper surface: Leathery; pubescent. Texture, lower surface: Leathery; glabrous. Color: Developing foliage, upper surface: 137B. Developing foliage, lower surface: 144A. Fully expanded foliage, upper surface: 137A. Fully expanded foliage, lower surface: 137B to 137C. Venation, upper and lower surfaces: 144B. Petiole: Length: About 4.8 cm. Diameter: About 3 mm. Texture, upper and lower surfaces: Glabrous. Color, upper surface: 144A to 144B. Color, lower surface: 144A.

Inflorescence description:

*Appearance.*—Terminal and axillary inflorescences held above and beyond the foliage. Composite inflorescence form, radially symmetrical, with ligulate-shaped ray florets and disc florets massed at the center; ray and disc florets arranged acropetally on a capitulum. Inflorescences face upright or outwardly.

*Flowering response.*—Plants flower continuous and freely from the spring through the summer. Early flowering, plants begin to flower about six weeks after planting.

*Postproduction longevity.*—Inflorescences maintain good color and substance for about three days on the plant. Inflorescences not persistent.

*Quantity of inflorescences.*—Freely flowering; about 30 to 35 open inflorescences and inflorescence buds per plant.

*Fragrance.*—None detected.

*Inflorescence bud.*—Length: About 1.3 cm. Diameter: About 1 cm. Shape: Ovoid. Color: 137B and 144C.

*Inflorescence size.*—Diameter: About 6.2 cm. Depth (height): About 2.9 cm. Disc diameter: About 1.4 cm. Receptacle diameter: About 4 mm. Receptacle height: About 3 mm.

*Ray florets.*—Length: About 3.3 cm. Width: About 8 mm. Shape: Elongated oblong. Apex: Emarginate. Base: Obtuse. Margin: Entire. Texture, upper and lower surfaces: Smooth, glabrous. Number of ray florets per inflorescence: About 18 to 20 in one to two whorls. Color: When opening and fully opened, upper surface: 12B. When opening and fully opened, lower surface: Ground color, 3A; longitudinal stripes, close to 137C.

*Disc florets.*—Shape: Tubular, elongated. Apex: Five-pointed. Length: About 5 mm. Width: At apex: About 2 mm. At base: Less than 1 mm. Number of disc florets per inflorescence: About 50. Color, apex: Close to 97B. Color, mid-section and base: Close to 155A to 157A.

*Phyllaries.*—Length: About 1.2 cm. Diameter: About 1.5 mm. Shape: Lanceolate. Apex: Apiculate. Base: Acute. Margin: Entire. Texture, upper and lower surfaces: Leathery. Number per inflorescence: About 16. Color, upper surface: 137B to 137C. Color, lower surface: 137C.

*Peduncles.*—Length, terminal peduncle: About 5.25 cm. Diameter: About 2 mm. Strength: Strong. Texture: Leathery. Color: 144A.

*Reproductive organs.*—Androecium: Present on disc florets only. Stamen number: Five per floret; fused around style. Anther shape: Oblong. Anther length: About 2 mm. Anther color: 79A to 79B. Pollen amount: Abundant. Pollen color: 23A. Gynoecium: Present on both ray and disc florets. Pistil number: One per floret. Pistil length: About 7 mm. Stigma shape: Two-parted. Stigma color: 79A and 4D. Style length: About 3 mm. Style color: 4D. Ovary color: 144C.

*Seed.*—Length: About 7 mm. Diameter: About 3 mm. Color: 199A.

Disease/pest resistance: Resistance to pathogens and pests common to *Osteospermums* has not been observed on plants grown under commercial greenhouse or outdoor conditions.

Temperature tolerance: Plants of the new *Osteospermum* have been observed to tolerate temperatures from about 5° C. to about 35° C.

It is claimed:

1. A new and distinct cultivar of *Osteospermum* plant named 'Duetisuneye', as illustrated and described.

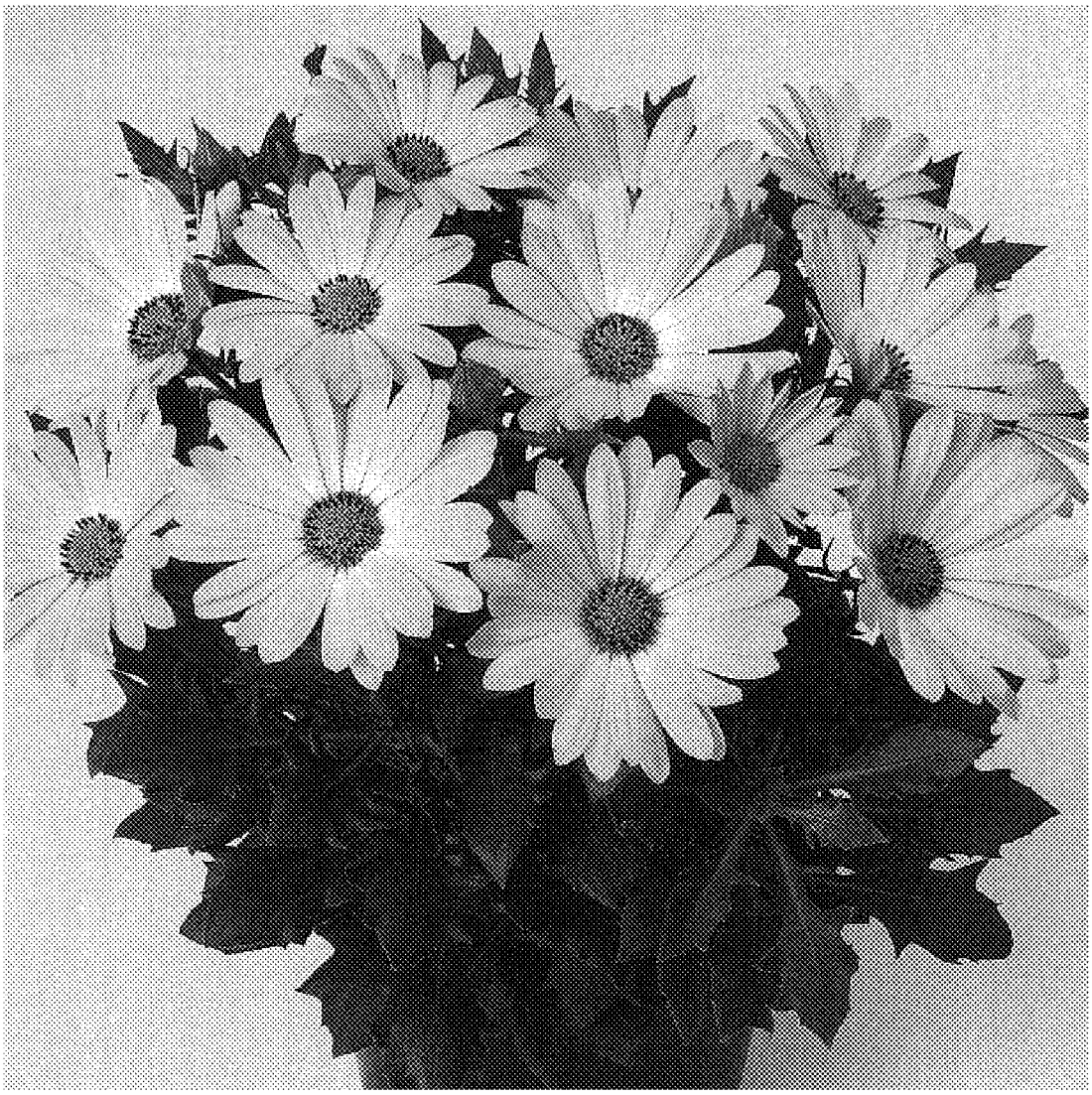

* * * * *